United States Patent [19]

Chu

[11] 4,391,739

[45] Jul. 5, 1983

[54] ZEOLITE CATALYSTS MODIFIED WITH GROUP IA METALS

[75] Inventor: Chin-Chiun Chu, North Brunswick, N.J.

[73] Assignee: Mobil Oil Corporation, New York, N.Y.

[21] Appl. No.: 339,960

[22] Filed: Jan. 18, 1982

Related U.S. Application Data

[63] Continuation-in-part of Ser. No. 146,951, May 5, 1980, Pat. No. 4,329,533.

[30] Foreign Application Priority Data

Feb. 19, 1981 [EP]  European Pat. Off. ........ 81300672.3

[51] Int. Cl.$^3$ .......................... B01J 29/28; B01J 27/18
[52] U.S. Cl. ................................ 252/455 Z; 252/437
[58] Field of Search ............................ 252/455 Z, 437

[56] References Cited

U.S. PATENT DOCUMENTS

| 4,115,424 | 9/1978 | Unland et al. | 252/455 Z |
| 4,218,573 | 8/1980 | Tabak et al. | 252/455 Z |
| 4,263,129 | 4/1981 | Chen | 252/455 Z |
| 4,274,982 | 6/1981 | Chu | 252/455 Z |

Primary Examiner—Carl F. Dees
Attorney, Agent, or Firm—Charles A. Huggett; Ronald J. Cier; George W. Allen

[57] ABSTRACT

A zeolite catalyst composition suitable for para-selective conversion of substituted aromatic compounds, e.g., to dialkylbenzene compounds rich in the 1,4-dialkylbenzene isomer. Such a composition comprises a zeolite catalyst having a silica to alumina mole ratio of at least 12 and a constraint index of about 1-12, and a minor amount, e.g., at least at 0.25 weight percent of one or more of the alkali metals (e.g., Li, Na, K, Cs) and optionally phosphorus, said alkali metals and phosphorus being present in the catalyst at least in part in the form of their oxides.

11 Claims, No Drawings

ZEOLITE CATALYSTS MODIFIED WITH GROUP IA METALS

CROSS-REFERENCE TO RELATED APPLICATION

This application is a continuation-in-part of the application of Chin-Chiun Chu, having Ser. No. 146,951, filed May 5, 1980 now U.S. Pat. No. 4,329,533.

BACKGROUND OF THE INVENTION

1. Field of the Invention

The invention disclosed herein relates to novel zeolite catalyst compositions which are particularly useful for the production of dialkylbenzene compound product mixtures in which the 1,4-dialkylbenzene isomer content is substantially in excess of its normal equilibrium concentration.

2. Description of the Prior Art

The disproportionation of aromatic hydrocarbons in the presence of zeolite catalysts has been described by Grandio et al. in the OIL AND GAS JOURNAL, Vol. 69, Number 48(1971).

U.S. Pat. Nos. 3,126,422; 3,413,374; 3,598,878; 3,598,879 and 3,607,961 show vapor-phase disproportionation of toluene over various catalysts.

In these prior art processes, the dimethylbenzene product produced has the equilibrium composition of approximately 24 percent of 1,4-, 54 percent of 1,3- and 22 percent of 1,2-isomer. Of the dimethylbenzene isomers, 1,3-dimethylbenzene is normally the least desired product, with 1,2- and 1,4-dimethylbenzene being the more useful products. 1,4-Dimethylbenzene is of particular value, being useful in the manufacture of terephthalic acid which is an intermediate in the manufacture of synthetic fibers such as "Dacron". Mixtures of dimethylbenzene isomers, either alone or in further admixture with ethylbenzene, have previously been separated by expensive superfractionation and multistage refrigeration steps. Such process, as will be realized, involves high operation costs and has a limited yield.

Various modified zeolite catalysts have been developed to alkylate or disproportionate toluene with a greater or lesser degree of selectivity to 1,4-dimethylbenzene isomer. Hence, U.S. Pat. Nos. 3,972,832, 4,034,053, 4,128,592 and 4,137,195 disclose particular zeolite catalysts which have been treated with compounds of phosphorus and/or magnesium. Boron-containing zeolites are shown in U.S. Pat. No. 4,067,920 and antimony-containing zeolites in U.S. Pat. No. 3,979,472. Similarly, U.S. Pat. Nos. 3,965,208 and 4,117,026 disclose other modified zeolites useful for shape selective reactions. It is also known to incorporate various metals into zeolite catalysts by means of ion exchange.

While the above-noted prior art is considered of interest in connection with the subject matter of the present invention, crystalline zeolite catalysts of specified characteristics which have undergone the particular treatment disclosed, have not, insofar as is known, been previously described.

SUMMARY OF THE INVENTION

In accordance with the present invention, there have now been discovered zeolite catalyst compositions modified in a particular manner with a Group IA metal, said composition being useful for conversion of substituted aromatic hydrocarbon compounds. An especially advantageous reaction promoted by the catalysts of this invention comprises the selective production of the 1,4-isomer of dialkylated benzene compounds. Such a process involves contacting an alkylated aromatic compound, either alone or in admixture with a suitable alkylating agent such as a methanol or ethylene, with the particular type of modified crystalline zeolite catalyst disclosed herein and under suitable conversion conditions to effect disproportionation or transalkylation of alkylbenzene compounds or alkylation of aromatic compounds to selectively produce the 1,4-dialkylbenzene isomer in excess of its normal equilibrium concentration.

The particular type of crystalline zeolite catalysts utilized herein comprise zeolite materials having a silica to alumina ratio of at least about 12 and a constraint index within the approximate range of 1 to 12. Such catalyst compositions are modified prior to catalytic use by initial treatment to replace the original cations therein with hydrogen or a hydrogen precursor and by subsequent treatment with one or more compounds derived from one or more of the elements of Group IA of the Periodic Table (or Periodic Chart) of Elements (i.e. the alkali metals: Li, Na, K, Rb and Cs) to yield a composite containing a minor proportion of an oxide of such element. In addition to treatment of the catalyst with the alkali metal-containing compound, the zeolite compositions may also be treated with a phosphorus-containing compound to deposit a minor proportion of an oxide of phosphorus thereon in addition to the oxide of the Group IA metal.

Such catalysts can be employed for the alkylation of aromatic compounds to realize selective production of the 1,4-dialkylbenzene isomer in preference to the 1,2- and 1,3- isomers thereof. Especially preferred processes involve the selective production of 1,4-dimethylbenzene from toluene and methanol and 1-ethyl-4-methylbenzene from toluene and ethylene.

Such catalysts can also be employed to realize the selective disproportionation or transalkylation of alkylbenzene and polyalkylbenzene compounds in the presence of the disclosed catalysts, thereby yielding 1,4-disubstituted benzenes in excess of their normal equilibrium concentration. For example, under appropriate conditions of temperature and pressure, toluene will disproportionate in the presence of these catalysts to produce benzene and dimethylbenzenes mixture enriched in the desirable 1,4-isomer.

DESCRIPTION OF SPECIFIC EMBODIMENTS

The crystalline zeolites of the present invention are members of a particular class of zeolitic materials which exhibit unusual properties. Although these zeolites have unusually low alumina contents, i.e. high silica to alumina mole ratios, they are very active even when the silica to alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this particular class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with silica to alumina mole ratios of at least 12 are useful, it is preferred in some instances to use zeolites having substantially higher silica/alumina ratios, e.g. 1600 and above. In addition, zeolites as otherwise characterized herein but which are substantially free of aluminum, that is zeolites having silica to alumina mole ratios of up to infinity, are found to be useful and even preferable in some instances. Such "high silica" or "highly siliceous" zeolites are intended to be included within this description. Also included within this definition are substantially pure silica forms of the useful zeolites described herein, that is to say those zeolites having no measurable amount of aluminum (silica to alumina mole ratio of infinity) but which otherwise embody the characteristics disclosed.

This particular class of zeolites, after activation, acquire an intracrystalline sorption capacity for normal hexane which is greater than that for water, i.e. they exhibit "hydrophobic" properties. This hydrophobic character can be used to advantage in some applications.

This particular class of zeolites useful herein have an effective pore size such as to freely sorb normal hexane. In addition, the structure must provide constrained access to larger molecules. It is sometimes possible to judge from a known crystal structure whether such constrained access exits. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons and, therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly spaced velocity of less than one, such as 0.1 or less, can be employed in order to achieve a minimum total conversion of about 10%.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical materials are:

|  | C.I. |
|---|---|
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 0.6 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than an exclusive value. That is, a crystalline zeolite when identified by any combination of conditions within the testing definition set forth herein as having a Constraint Index in the range of 1 to 12 is intended to be included in the instant zeolite definition whether or not the same identical zeolite, when tested under other of the defined conditions, may have a Constraint Index value outside of the range of 1 to 12.

The particular class of zeolites defined herein is exemplified by ZSM-5, ZSM-11, ZSM-12, ZSM-23, ZSM-35, ZSM-38, ZSM-48 and other similar materials.

ZSM-5 is described in greater detail in U.S. Pat. No. 3,702,886 and Re No. 29,948. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,046,859. The description of that zeolite, and particularly the specified X-ray diffraction pattern thereof, is incorporated herein by reference.

ZSM-48 can be identified, in terms of moles of anhydrous oxides per 100 moles of silica, as follows:

(0–15)RN:(0–1.5)M$_{2/n}$O:(0–2)Al$_2$O$_3$:(100)SiO$_2$ wherein:

M is at least one cation having a valence n; and
RN is a C$_1$–C$_{20}$ organic compound having at least one amine functional group of pK$_a \geq 7$.

It is recognized that, particularly when the composition contains tetrahedral, framework aluminum, a fraction of the amine functional groups may be protonated. The doubly protonated from, in conventional notation, would be (RNH)$_2$O and is equivalent in stoichiometry to 2RN+H$_2$O.

The characteristic X-ray diffraction pattern of the synthetic zeolite ZSM-48 has the following significant lines:

Characteristic Lines of ZSM-48

| d (Angstroms) | Relative Intensity |
| --- | --- |
| 11.9 | W–S |
| 10.2 | W |
| 7.2 | W |
| 5.9 | W |
| 4.2 | VS |
| 3.9 | VS |
| 3.6 | W |
| 2.85 | W |

These values were determined by standard techniques. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, 100 I/I$_o$, where I$_o$ is the intensity of the strongest line or peak, and d (obs.), the interplanar spacing in Angstroms, corresponding to the recorded lines, were calculated. In the foregoing table the relative intensities are given in terms of the symbols W=weak, VS=very strong and W-S=weak-to-strong. Ion exchange of the sodium ion with cations reveals substantially the same pattern with some minor shifts in interplanar spacing and variation in relative intensity. Other minor variations can occur depending on the silicon to aluminum ratio of the particular sample, as well as if it has been subjected to thermal treatment.

The ZSM-48 zeolite can be prepared from a reaction mixture containing a source of silica, water, RN, an alkali metal oxide (e.g. sodium) and optionally alumina. The reaction mixture should have a composition, in terms of mole ratios of oxides, falling within the following ranges:

| REACTANTS | BROAD | PREFERRED |
| --- | --- | --- |
| Al$_2$O$_3$/SiO$_2$ | = 0 to 0.02 | 0 to 0.01 |
| Na/SiO$_2$ | = 0 to 2 | 0.1 to 1.0 |
| RN/SiO$_2$ | = 0.01 to 2. | 0.05 to 1.0 |
| OH$^-$/SiO$_2$ | = 0 to 0.25 | 0 to 0.1 |
| H$_2$O/SiO$_2$ | = 10 to 100 | 20 to 70 |
| H$^+$(added)/SiO$_2$ | = 0 to 0.2 | 0 to 0.05 | wherein RN is a C$_1$–C$_{20}$ organic compound having amine functional group of pK$_a \geq 7$. The mixture is maintained at 80°–250° C. until crystals of the material are formed. H$^+$(added) is moles acid added in excess of the moles of hydroxide added. In calculating H$^+$(added) and OH values, the term acid (H$^+$) includes both hydronium ion, whether free or coordinated, and aluminum. This aluminum sulfate, for example, would be considered a mixture of aluminum oxide, sulfuric acid, and water. An amine hydrochloride would be a mixture of amine and HCl. In preparing the highly siliceous form of ZSM-48 no alumina is added. Thus, the only aluminum present occurs as an impurity in the reactants.

Preferably, crystallization is carried out under pressure in an autoclave or static bomb reactor, at 80° C. to 250° C. Thereafter, the crystals are separated from the liquid and recovered. The composition can be prepared utilizing materials which supply the appropriate oxide. Such compositions include sodium silicate, silica hydrosol, silica gel, silicic acid, RN, sodium hydroxide, sodium chloride, aluminum sulfate, sodium aluminate, aluminum oxide, or aluminum itself. RN is a $C_1$-$C_{20}$ organic compound containing at least one amine functional group of $pK_a \geq 7$, as defined above, and includes such compounds as $C_3$-$C_{18}$ primary, secondary, and tertiary amines, cyclic amine (such as piperidine, pyrrolidine and piperazine), and polyamines such as $NH_2$—$C_nH_{2n}$—$NH_2$ were n is 4-12.

In all of the foregoing zeolites, the original cations can be subsequently replaced, at least in part, by calcination and/or ion exchange with another cation. Thus, the original cations can be exchanged into a hydrogen or hydrogen ion precursor form or a form in which the original cations have been replaced by a metal of, for example, Groups II through VIII of the Periodic Table. Thus, it is contemplated to exchange the original cations with ammonium ions or with hydronium ions. Catalytically active forms of these would include, in particular, hydrogen, rare earth metals, aluminum, manganese and other metals of Groups II and VIII of the Periodic Table.

It is to be understood that by incorporating by reference the foregoing patents to describe examples of specific members of the specified zeolite class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intra-crystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38, and ZSM-48, with ZSM-5 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired for several reasons. When hydrocarbon products or by-products are catalytically formed, for example, such zeolites tend to maximize the production of gasoline boiling range hydrocarbon products. Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1976) published by the Society of Chemical Industry, London, 1968.

When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |

| -continued | | |
|---|---|---|
| | Void Volume | Framework Density |
| Y | .48 | 1.27 |

When synthesized in the alkali metal form, the zeolite can be conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used as precursors to the alkali metal oxide modified zeolite compositions of the present invention. Thus, the original alkali metal of the zeolite may be replaced by ion exchange with other suitable metal cations of Groups I through VIII of the Periodic Table, including, by way of example, nickel, copper, zinc, palladium, calcium or rare earth metals. As discussed more fully hereinafter, incorporation of metal by ion exchange can contribute to the modification of the zeolite compositions herein with alkali metals.

In practicing any given desired hydrocarbon conversion process, it may be useful to incorporate the above-described crystalline zeolites with a matrix comprising another material resistant to the temperature and other conditions employed in the process in order to thereby form the complete catalyst composition. Such matrix material is useful as a binder and imparts greater resistance to the catalyst for the severe temperature, pressure and reactant feed stream velocity conditions encountered, for example, in many hydrocarbon conversion processes.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

The zeolite catalyst compositions as described herein are, in accordance with the present invention, modified by incorporating thereon a minor amount of one or more of the alkali metal elements of Group IA of the Periodic Chart of the Elements, in the form of an alkali metal oxide. The Periodic Chart referred to herein is that version published by the Fisher Scientific Company (Cat. No. 5-702-10), the alkali metal elements of Group IA being lithium (Li), sodium (Na), potassium (K), rubidium (Rb) and cesium (Cs).

These alkali metals, as well as other optional components described hereinafter, can generally be incorporated by contacting the zeolite composition with a treating medium, e.g., a solution, containing the elements or one or more compounds of the elements to be incorporated. Incorporation can occur by the mechanisms of ion exchange, adsorption and/or impregnation, the latter two phenomena commonly being referred to as "stuffing". It should be emphasized that, while ion exchange can be used to incorporate some of the alkali or other metals onto the zeolite compositions described herein, ion exchange alone will generally not provide the requisite amount or form of incorporated alkali metal onto the zeolite catalyst composition of the present invention. It should thus be noted that at least some alkali metal over and above that incorporated by ion exchange should be incorporated into the zeolite by "stuffing" techniques. This insures that the alkali metal associated with the zeolite will be, at least in part, present in its oxide form as hereinafter more fully described. Combinations of incorporation techniques may also be employed, for example, by incorporating one element by ion exchange and another element by stuffing.

Solutions of compounds of alkali metals, as well as of other elements to be incorporated onto the zeolite catalyst, may be formulated from any suitable solvent which is inert with respect to the compound to be incorporated and the zeolite. Non-limiting examples of some suitable solvents include water, aliphatic and aromatic hydrocarbons, alcohols, organic acids (such as acetic acid, formic acid, propionic acid and so forth), and inorganic acids (such as hydrochloric acid, sulfuric acid and nitric acid). Other commonly available solvents such as halogenated hydrocarbons, ketones, ethers, etc. may be useful to dissolve some metal compounds or complexes. Generally, the most useful solvent will be found to be water. However, the solvent of choice for any particular compound will, of course, be determined by the nature of the compound and for that reason the foregoing list should not be considered exhaustive of all of the suitable possibilities.

Representative lithium-containing compounds which can be used for incorporating lithium into the zeolite-based compositions herein include lithium acetate, lithium acetylsalicylate, lithium carbonate, lithium chlorate, lithium perchlorate, lithium chloride, lithium bromide, lithium fluoride, lithium iodide, lithium iodate, lithium nitrite, lithium nitrate, lithium oxalate, lithium palmitate, lithium salicylate, lithium sulfate, lithium tartarate, lithium sulfide, lithium thiocyanate and lithium stearate. This listing is not to be taken as encompassing all of the utilizable lithium-containing compounds. It is merely intended to be illustrative of some of the representative metal compounds which those in the art will find useful in practicing the disclosed invention. The knowledgeable reader will readily appreciate that there are numerous other known lithium salts and complexes which would provide solutions containing lithium suitable for combination with the zeolite in the manner hereinafter described.

Reaction of the zeolite composite with the treating lithium compound is effected by contacting the zeolite with such compound. Where the treating compound is a liquid, such compound can be, as noted, in solution in a solvent at the time contact with the zeolite is effected. Any solvent relatively inert with respect to the treating lithium compound and the zeolite may be employed. Suitable solvents include water and aliphatic, aromatic or alcoholic liquids. The treating compound may also be used without a solvent, i.e. may be used as a neat liquid. Where the treating compound is in the aqueous phase, it can be used by itself or in admixture with a gaseous diluent relatively inert to the treating compound and the zeolite (such as helium or nitrogen) or with an organic solvent such as octane or toluene.

Heating of the lithium compound containing catalyst subsequent to preparation and prior to use is preferred, and such heating can generally be carried out in the presence of oxygen, for example, in air. Although heating may be carried out at a temperature of about 150° C. or more, higher temperatures, e.g. up to about 500° C., are preferred. Heating is generally carried out for 1–5 hours but may be extended to 24 hours or longer. While heating temperatures above about 500° C. may be employed, they are generally not necessary. After heating in air at elevated temperatures, and without being limited by any theoretical considerations, it is contemplated that the lithium is actually present in the zeolite at least in part in an oxidized state, such as $Li_2O$.

The amount of lithium oxide incorporated in the zeolite should be at least about 0.25 percent by weight, calculated on the basis of elemental lithium. However, it is preferred that the amount utilized be at least about 1.0 percent by weight, calculated on the basis of elemental lithium, particularly when the zeolite is combined with a binder, e.g. 35 weight percent of alumina. The amount of lithium oxide can be as high as about 15 percent by weight or more, calculated on the basis of elemental lithium, depending on the amount and type of binder present. Preferably, the amount of lithium oxide added to the zeolite will be between about 1 and about 10 percent by weight, calculated on the basis of elemental lithium.

The amount of lithium oxide incorporated with the zeolite composite will depend upon several factors. One of these is the reaction time, i.e., the time that the zeolite and the lithium-containing source are maintained in contact with each other. With greater reaction times, all other factors being equal, a greater amount of metal is incorporated with the zeolite. Other factors upon which the amount of lithium incorporated with the zeolite is dependent include reaction temperature, concentration of the treating agent in the reaction mixture, the degree to which the zeolite has been dried prior to reaction with the metal-containing compound, the conditions of drying of the zeolite after reaction with the treating compound, and the amount and type of binder incorporated with the zeolite composite.

Oxides of sodium are also effective modifying components for imparting the desirable shape selective activity to the particular type of zeolite composites disclosed. Examples of representative sodium-containing compounds suitable for incorporation of that metal with the zeolite composites herein include sodium acetate, sodium barbital, sodium benzoate, sodium carbonate, sodium chloride, sodium chlorate, sodium bromide, sodium bromate, sodium perchlorate, sodium chlorite, sodium hypochlorite, sodium cinnamate, sodium citrate, sodium cyanate, sodium cyanide, sodium ethylacetoacetate, sodium hydride, sodium hydrogen fluoride, sodium formate, sodium glutamate, sodium iodide, sodium iodate, sodium periodate, sodium hydroxide, sodium lactate, sodium methoxide, sodium ethoxide, sodium nitrate, sodium nitrite, sodium oleate, sodium oxalate, sodium palmitate, sodium phenoxide, sodium carbonate, sodium bicarbonate, sodium propionate, sodium salicylate, sodium stearate, sodium succinate, sodium sulfate, sodium persulfate, sodium hydrogen sulfate, sodium hydrogen sulfide, sodium sulfide, sodium sulfite, sodium tartarate, sodium thiocyanate, sodium thiosulfate, and sodium ammonium tartarate. As discussed above with respect to the illustrative listing of lithium compounds, the foregoing is not to be considered as an exhaustive list of the utilizable sodium salts and complexes. There are numerous sodium compounds which the foregoing will suggest to those skilled in the art as being suitable for providing, for example, the sodium-containing solutions for treatment of the zeolite as hereinafter described.

Reaction of the zeolite with the sodium compounds is accomplished in substantially the same way as that recited above with respect to the lithium-containing compounds. Without being limited by any theoretical considerations, it is contemplated that the sodium is likewise present in the modified zeolite at least in part in an oxidized state, such as $Na_2O$.

The amount of sodium oxide incorporated with the zeolite composite should be at least about 0.25 percent by weight, calculated on the basis of elemental sodium. However, it is preferred that the amount utilized comprise at least about 1.0 percent by weight calculated on the basis of elemental sodium, particularly when the zeolite is combined with a binder, e.g. 35 weight percent of alumina. The amount of sodium oxide can be as high as about 15 percent by weight or more calculated as elemental sodium, depending on the amount and type of binder present. Preferably, the amount of sodium oxide added to the zeolite will be between about 1.0 and about 15 percent by weight, calculated on the basis of elemental sodium.

Oxides of potassium may also be employed as a catalyst modifying component. The potassium oxide is contemplated as being present as $K_2O$ alone or in combination with other compounds of potassium in an oxidized state. In all instances, regardless of the particular state of oxidation of the potassium, its content with respect to the zeolite is computed on the basis of elemental potassium. Generally, the amount of $K_2O$ in the composite catalyst will be between about 0.25 and about 20 weight percent calculated on the basis of elemental potassium, and preferably between about 1.0 and about 15 weight percent calculated on the basis of elemental potassium and based on the weight of the composite. Reaction of the zeolite with the potassium-containing compound is carried out as described above with respect to the treatment with compounds of the element lithium.

Examples of potassium compounds which may be utilized include potassium acetate, potassium acetyl salicylate, potassium bromide, potassium bromate, potassium chloride, potassium camphorate, potassium carbonate, potassium chloride, potassium chlorate, potassium perchlorate, potassium hypochlorite, potassium chloroiodate, potassium citrate, potassium cyanate, potassium cyanide, potassium ethylsulfate, potassium hydride, potassium fluoride, potassium hydroxide, potassium iodate, potassium iodide, potassium lactate, potassium laurate, potassium malate, potassium methylsulfate, potassium nitrate, potassium nitrite, potassium oleate, poassium oxalate, potassium picrate, potassium phthalate, potassium piperate, potassium sorbate, potassium stearate, potassium sulfate, potassium succinate, potassium pyrosulfate, potassium sulfide, potassium hydrogen sulfide, potassium sulfite, potassium tartarate, potassium thiocyanate, potassium dithionate, and potassium xanthate. Again, this listing is not intended to be exhaustive, but rather suggestive to those of skill in the art as to the kinds of metal-containing compounds useful for treating the zeolite composite as herein described.

A further embodiment contemplates incorporation of oxides of cesium with the zeolite composite as the modifying component. The cesium oxide is contemplated as being present as $Cs_2O$ alone or in combination with other compounds of cesium in an oxidized state. In all instances, regardless of the particular state of oxidation of the cesium, its content with respect to the zeolite composite is computed on the basis of elemental cesium. Generally, the amount of $Cs_2O$ in the composite catalyst will be between about 0.25 and about 35 weight percent, and preferably between about 1.0 and about 30 weight percent, calculated on the basis of elemental cesium and based on the weight of the composite. Reaction of the zeolite with the cesium-containing compound is carried out as described above with respect to the treatment with compounds of the element lithium.

Examples of cesium compounds which may be utilized include cesium acetate, cesium benzoate, cesium bromide, cesium bromate, cesium carbonate, cesium hydrogen carbonate, cesium chloride, cesium chlorate, cesium perchlorate, cesium fluoride, cesium formate, cesium hydride, cesium hydroxide, cesium iodide, cesium iodate, cesium periodate, cesium nitrate, cesium nitrite, cesium oxalate, cesium oxide, cesium salicylate, cesium sulfate, cesium sulfide, cesium tartarate, and cesium hydrogen tartarate. As before, it is cautioned that this listing is intended as suggestive to those of skill in the art as to the general kinds of cesium-containing compounds which they will find useful in practicing the herein disclosed invention.

In some instances, it may be desirable to modify the crystalline zeolites by combining therewith two or more of the specified alkali metal oxides. Thus, the zeolite may be modified by prior combination therewith of oxides of lithium and sodium, oxides of lithium and potassium, lithium and rubidium, lithium and cesium, sodium and potassium, sodium and rubidium, sodium and cesium, potassium and rubidium, potassium and cesium, rubidium and cesium, or even ternary or higher combinations. When such modification technique is employed, the respective oxides may be deposited on the zeolite either sequentially or from a solution containing suitable compounds of the elements, the oxides of which are to be combined with the zeolite. The amounts of oxides present in such instance are in the same range as specified above for the individual oxides, with the overall added oxide content being between about 1 and about 40 weight percent of the composite calculated on the basis of total elemental alkali metal.

A further embodiment of this invention includes additional modification of the above metal oxide-zeolite composites with phosphorus, whereby from about 0.25 weight percent to about 30 weight percent of an oxide of phosphorus, calculated as elemental phosphorus, is combined with the zeolite. The preferred amount of phosphorus oxide will be between about 1.0 weight percent and about 25 weight percent calculated as elemental phosphorus and based on the weight of the treated zeolite. The phosphorus treatment of the zeolite catalyst will preferably be carried out before the previously described modification with Group IA metals. Reaction of the zeolite compound with the phosphorus-containing compound is carried out essentially as described above with respect to the metal-containing compounds and it is preferred that the total amount of oxides combined with the zeolite, i.e. the phosphorus oxides plus the metal oxides, fall within the approximate range of 2 percent to 35 percent by weight, based on the weight of the treated zeolite and calculated on the basis of elemental phosphorus and elemental alkali metal.

Representative phosphorus-containing compounds which may be used include derivatives of groups represented by $PX_3$, $RPX_2$, $R_2PX$, $R_3P$, $X_3PO$, $(XO)_3PO$, $(XO)_3P$, $R_3P=O$, $R_3P=S$, $RPO_2$, $RPS_2$, $RP(O)(OX)_2$, $RP(S)(SX)_2$, $R_2P(O)OX$, $R_2P(S)SX$, $RP(SX)_2$, $ROP(OX)_2$, $RSP(SX)_2$, $(RS)_2PSP(SR)_2$, and $(RO)_2POP(OR)_2$, where R is an alkyl or aryl, such as a phenyl radical and X is hydrogen, R, or halide, These compounds include primary, $RPH_2$, secondary, $R_2PH$ and tertiary, $R_3P$, phosphines such as butyl phosphine; the tertiary phosphine oxides $R_3PO$, such as tributylphosphine oxide, the tertiary phosphine sulfides, $R_3PS$, the primary, $RP(O)(OX)_2$, and secondary, $R_2P(O)OX$, phosphonic acids such as benzene phosphonic acid; the corresponding sulfur derivatives such as $RP(S)(SX)_2$ and $R_2P(S)SX$, the esters of the phosphonic acids such as diethyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2POX$, such ad diethylphosphinous acid, primary, $(RO)P(OX)_2$, secondary, $(RO)_2POX$, and tertiary, $(RO)_3P$, phosphites; and esters thereof such as the monopropyl ester, alkyl dialkylphosphinites, $(RO)PR_2$, and dialkyl alkylphosphinite, $(RO)_2PR$ esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$ and $(RS)_2PR$. Examples of phosphite esters include trimethylphosphite, triethylphosphite, diisopropylphosphite, butylphosphite; and pyrophosphites such as tetraethylpyrophosphite. The alkyl groups in the mentioned compounds contain from one to four carbon atoms.

Other suitable phosphorus-containing compounds include the phosphorus halides such as phosphorus trichloride, bromide, and iodide, alkyl phosphorodichloridites, $(RO)PCl_2$, dialkyl phosphorochloridites, $(RO)_2PCl$, dialkylphosphinochloridites, $R_2PCl$, alkyl alkylphosphonochloridates, $(RO)(R)P(O)Cl$, dialkyl phosphinochloridates, $R_2P(O)Cl$ and $RP(O)Cl_2$. Applicable corresponding sulfur derivatives include $(RS)PCl_2$, $(RS)_2PCl$, $(RS)(R)P(S)Cl$ and $R_2P(S)Cl$.

Preferred phosphorus-containing compounds include diphenyl phosphine chloride, trimethylphosphite and phosphorus trichloride, phosphoric acid, phenyl phosphine oxychloride, trimethylphosphate, diphenyl phosphinous acid, diphenyl phosphinic acid, diethylchlorothiophosphate, methyl acid phosphate and other alcohol-$PO_5$ reaction products.

Particularly preferred are ammonium phosphates, including ammonium hydrogen phosphate, $(NH_4)_2HPO_4$, and ammonium dihydrogen phosphate, $NH_4H_2PO_4$.

Another optional modifying treatment entails steaming of the zeolite by contact with an atmosphere containing from about 5 to about 100 percent steam at a temperature of from about 250° to about 1000° C. for a period of between about 15 minutes and about 100 hours and under pressures ranging from sub-atmospheric to several hundred atmospheres. Preferably, steam treatment is effected at a temperature of between about 400° C. and about 700° C. for a period of between about 1 and about 24 hours.

Another optional modifying treatment involves precoking of the catalyst composite to deposit a coating of between about 2 and about 75, and preferably between about 15 and about 75, weight percent of coke thereon. Precoking can be accomplished by contacting the catalyst with a hydrocarbon charge, e.g. toluene, under high severity conditions or alternatively at a reduced hydrogen to hydrocarbon concentration, i.e. 0 to 1 mole ratio of hydrogen to hydrocarbon, for a sufficient time to deposit the desired amount of coke thereon.

It is also contemplated that a combination of steaming and precoking of the catalyst under the above conditions may be employed to suitably modify the crystalline zeolite catalyst.

Alkylation of aromatic compounds in the presence of the above-described catalysts can be effected by contact of the aromatic with an alkylating agent. A particularly preferred embodiment involves the alkylation of toluene wherein the alkylating agents employed comprise methanol or other well known methylating agents or ethylene. The reaction is carried out at a temperature of between about 250° C. and about 750° C., preferably between about 300° C. and 650° C. At higher temperatures, the zeolites of high silica/alumina ratio are preferred. For example, ZSM-5 having a $SiO_2/Al_2O_3$ ratio of 30 and upwards is exceptionally stable at high temperatures. The reaction generally takes place at atmospheric pressure, but pressures within the approximate range of $10^5$ N/m$^2$ to $10^7$ N/m$^2$ (1–100 atmospheres) may be employed.

Some non-limiting examples of suitable alkylating agents would include olefins such as, for example, ethylene, propylene, butene, decene and dodecene, as well as formaldehyde, alkyl halides and alcohols, the alkyl portion thereof having from 1 to 16 carbon atoms. Numerous other aliphatic compounds having at least one reactive alkyl radical may be utilized as alkylating agents.

Aromatic compounds which may be selectively alkylated as described herein would include any alkylatable aromatic hydrocarbon such as, for example, benzene, ethylbenzene, toluene, dimethylbenzenes, diethylbenzenes, methylethylbenzenes, propylbenzene, isopropylbenzene, isopropylmethylbenzenes, or substantially any mono- or di-substituted benzenes which are alkylatable in the 4-position of the aromatic ring.

The molar ratio of alkylating agent to aromatic compound is generally between about 0.05 and about 5. For instance, when methanol is employed as the methylating agent and toluene is the aromatic, a suitable molar ratio of methanol to toluene has been found to be approximately 1–0.1 moles of methanol per mole of toluene. Reaction is suitably accomplished utilizing a feed weight hourly space velocity (WHSV) of between about 1 and about 1000, and preferably between about 1 and about 200. The reaction product, consisting predominantly of the 1,4-dialkyl isomer, e.g. 1,4-dimethylbenzene, 1-ethyl-4-methylbenzene, etc., or a mixture of the 1,4- and 1,2-isomers together with comparatively smaller amounts of 1,3-dialkylbenzene isomer, may be separated by any suitable means. Such means may include, for example, passing the reaction product stream through a water condenser and subsequently passing the organic phase through a column in which chromatographic separation of the aromatic isomers is accomplished.

When transalkylation is to be accomplished, transalkylating agents are alkyl or polyalkyl aromatic hydrocarbons wherein alkyl may be composed of from 1 to about 5 carbon atoms, such as, for example, toluene, xylene, trimethylbenzene, triethylbenzene, dimethylethylbenzene, ethylbenzene, diethylbenzene, ethyltoluene, and so forth.

Another aspect of this invention involves the selective disproportionation of alkylated aromatic compounds to produce dialkylbenzene wherein the yield of 1,4-dialkyl isomer is in excess of the normal equilibrium concentration. In this context, it should be noted that disproportionation is a special case of transalkylation in which the alkylatable hydrocarbon and the transalkylating agent are the same compound, for example, when toluene serves as the donor and acceptor of a transferred methyl group to produce benzene and xylene.

The transalkylation and disproportionation reactions are carried out by contacting the reactants with the above-described modified zeolite catalyst at a temperature of between about 350° C. and 750° C. at a pressure of between atmospheric ($10^5$ N/m$^2$) and about 100 atmospheres ($10^7$ N/m$^2$). The reactant feed WHSV will normally fall within the range of about 0.1 to about 50. Preferred alkylated aromatic compounds suitable for utilization in the disproportionation embodiment comprise toluene, ethylbenzene, propylbenzene or substantially any mono-substituted alkylbenzene. These aromatic compounds are selectively converted to, respectively, 1,4-dimethylbenzene, 1,4-diethylbenzene, 1,4-dipropylbenzene, or other 1,4-dialkylbenzene, as appropriate, with benzene being a primary side product in each instance. The product is recovered from the reactor effluent by conventional means, such as distillation to remove the desired products of benzene and dialkylbenzene, and any unreacted aromatic component is recycled for further reaction.

The hydrocarbon conversion processes described herein may be carried out as a batch type, semi-continuous or continuous operation utilizing a fixed or moving bed catalyst system. The catalyst after use in a moving bed reactor is conducted to a regeneration zone wherein coke is burned from the catalyst in an oxygen-containing atmosphere, e.g. air, at an elevated temperature, after which the regenerated catalyst is recycled to the conversion zone for further contact with the charge stock. In a fixed bed reactor, regeneration is carried out in a conventional manner where an inert gas containing a small amount of oxygen (0.5–2%) is used to burn the coke in a controlled manner so as to limit the temperature to a maximum of around 500°–550° C.

The following examples will serve to illustrate certain specific embodiments of the hereindisclosed invention. These examples should not, however, be construed as limiting the scope of the novel invention as there are many variations which may be made thereon without departing from the spirit of the disclosed invention, as those of skill in the art will recognize.

EXAMPLE 1A

[Alkylation reaction with unmodified ZSM-5]

Five grams of HZSM-5 ($SiO_2/Al_2O_3$ mole ratio=70; 65% on alumina binder) were placed in a quartz flow reactor and heated to temperature. A feed stream of toluene and methanol, at a molar ratio of 4 to 1, was passed over the heated zeolite at a weight hourly space velocity (WHSV) of 10. The results obtained at various temperatures are shown below.

| Temperature °C. | Percent Toluene Conversion | Percent para xylene in xylenes |
|---|---|---|
| 350 | 47.2 | 24.8 |
| 400 | 58.0 | 24.4 |
| 450 | 68.0 | 24.3 |
| 500 | 87.6 | 24.2 |

EXAMPLE 1B

In a similar manner, toluene was alkylated with ethylene by passing toluene and ethylene at weight hourly space velocity 7.0 and 0.5, respectively, over the heated ZSM-5. The results at various temperatures are shown below.

| Temperature °C. | Percent Toluene Conversion | Isomer Ratios of Ethyltoluene | | |
|---|---|---|---|---|
| | | p | m | o |
| 400 | 76.4 | 29.9 | 58.5 | 11.6 |
| 425 | 76.4 | 29.9 | 57.5 | 12.7 |
| 450 | 79.0 | 29.6 | 57.1 | 13.4 |

EXAMPE 2

[Disproportionation reaction with unmodified ZSM-5]

Toluene was passed over 6 grams of the unmodified HZSM-5 zeolite of Example 1 at temperatures ranging between 450° C. and 600° C. The toluene feed WHSV was maintained at 3.5–3.6. The results are summarized below.

| Temperature °C. | WHSV | Toluene Conversion Mole % | % Selectivity, Wt. | | % Para in Xylene Products |
|---|---|---|---|---|---|
| | | | Benzene | Xylenes | |
| 450 | 3.6 | 7.4 | 43.5 | 55.5 | 24.7 |
| 500 | 3.5 | 20.5 | 44.6 | 53.8 | 24.5 |
| 550 | 3.5 | 38.8 | 48.0 | 48.8 | 24.2 |
| 600 | 3.5 | 49.2 | 54.4 | 41.7 | 24.1 |

EXAMPLE 3

[Preparation of Li-modified zeolite]

To a solution of 2.0 g lithium acetate in 5.0 ml water heated at 80° C. was added 2.5 g HZSM-5 with $SiO_2/Al_2O_3=70$. The mixture was maintained at 70°–80° C. for 2 hours. After filtration and drying at about 90° C. for 2 hours, the residue was calcined at 500° C. for an additional 2 hours to give 2.5 g of Li-ZSM-5. The content of lithium was found to be 2.47%.

EXAMPLE 4

[Alkylation reaction with Li-modified zeolite]

Alkylation of toluene with methanol was carried out by passing a toluene/methanol mixture in a molar ratio of 4/1 a WHSV=10 over 1.1 g of Li-ZSM-5 catalyst of Example 3 heated at 400° C. Toluene conversion was 7.6% and selectivity to p-xylene in xylenes was 72.3%, a three-fold increase over the selectivity demonstrated by the unmodified ZSM-5 of Example 1A.

EXAMPLE 5

[Preparation of Na-modified zeolite]

Mixed 2.0 g of HZSM-5 ($SiO_2/Al_2O_3=70$) with an 80° C. solution of 4.0 g sodium tartarate in 10 ml of water. The mixture was maintained at 80°–90° C. for 2 hours and then filtered to recover the zeolite. After drying at about 90° C. for 1 hour, followed by calcining at 500° C. for 2 hours more, there were 2.02 g of Na-ZSM-5 recovered. Upon analysis, the modified zeolite was found to contain 2.61% sodium.

EXAMPLE 6

[Alkylation reaction with Na-modified zeolite]

Alkylation of toluene with methanol was carried out by passing a toluene/methanol feed stream (molar ratio=4/1) over 1.1 g of the Na-ZSM-5 zeolite prepared in Example 5. The temperature was 600° C. and the feed rate (WHSV) was 10 $hr^{-1}$. Under these conditions of reaction toluene conversion was 3.0% with selectivity to the para-isomer in the xylene product at 62.2%. By contrast, the unmodified zeolite, in essentially the same reaction [Example 1A], yielded an equilibrium mixture of the three isomers.

EXAMPLE 7

[Disproportionation reaction with Na-modified zeolite]

Toluene disproportionation activity of the Na-ZSM-5 was tested by passing a stream of toluene over the catalyst at WHSV of 3.5 $hr^{-1}$ and a temperature of 500° C. Upon analysis of the reactor effluent it was found that 47.5% of the xylene produced was the para-isomer. This is approximately twice the level of para-selectivity found in Example 2 for the unmodified zeolite.

EXAMPLE 8

[Preparation of K-modified zeolite]

To a solution of 4.0 g potassium acetate in 10 ml The mixture was maintained at 20° C. for 4 hours. After filtration and drying at about 80° C. for 16 hours, the residue was calcined at 500° C. for an additional 2 hours to give 2.7 g of K-ZSM-5. The content of potassium was found to be 15.4%.

EXAMPLE 9A

[Alkylation reaction with K-modified zeolite]

Alkylation of toluene with methanol was carried out by passing a toluene/methanol mixture (molar ratio of 4/1) at WHSV=10 over 1.1 g of the K-ZSM-5 catalyst of Example 8 which had been heated at 500° C. Toluene conversion was 5.2% and selectivity to p-xylene in xylenes was 66.4%. When unmodified zeolite was employed in the same reaction (Example 1A), there was only a 24.2% selectivity to para-xylene.

EXAMPLE 9B

In a similar manner, alkylation of toluene was carried out by passing toluene (at WHSV=7) and ethylene (at WHSV=0.5) over 2.2 g of the K-ZSM-5 catalyst of Example 8 at 400° C. Conversion of toluene was 5.5% and selectivity to p-ethyltoluene in ethyltoluene was 80.0%. With the unmodified ZSM-5 (Example 1B) the same reaction resulted in only a 29.9% selectivity to para-isomer.

EXAMPLE 10

[Disproportionation reaction with K-modified zeolite]

Disproportionation of toluene was carried out by passing toluene over 1.1 g of the K-ZSM-5 catalyst of Example 8 at WHSV=3.5 and 500° C. Toluene conversion was 1.5% and selectivity to p-xylene in xylene was 60.8%. In contrast, the unmodified zeolite (Example 2) resulted in only 24.5% selectivity to the para-isomer under the same conditions.

EXAMPLE 11

[Preparation of Cs-modified zeolite]

One gram of cesium nitrate was dissolved in 10 ml of water. Added 1.5 g H-ZSM-5 ($SiO_2/Al_2O_3$=70) and maintained the mixture at 18° C. for 5 hours. After recovering the zeolite by filtration and drying at about 90° C. for 16 hours, it was calcined at 500° C. for an additional 24 hours. The resultant Cs-ZSM-5 was found to contain 12.4% cesium.

EXAMPLE 12A

[Alkylation reaction with Cs-modified zeolite]

Alkylation of toluene with methanol at 600° C. was carried out by passing a toluene/methanol (molar ratio 4/1) mixture over 1.1 g of the Cs-ZSM-5 zeolite of Example 11 at WHSV of 10 $hr^{-1}$. Toluene conversion was found to be 11.6% and selectivity to para-isomer in the xylene product was 57.6%. Again, this is more than a two-fold increase over the equilibrium mixture which results for use of the unmodified zeolite [Example 1A].

EXAMPLE 12B

In a similar manner, ethylation of toluene was carried out by passing toluene (at WHSV=7 $hr^{-1}$) and ethylene (at WHSV=0.5 $hr^{-1}$) over 1.1 g of the Cs-ZSM-5 zeolite at 400° C. Toluene conversion was 2.7% and selectivity to para-ethyltoluene in the ethyltoluene produced was 60.0%. The unmodified ZSM-5 had only a 29.9% para-selectivity under the same conditions of reaction [Example 1B].

EXAMPLE 13

[Disproportionation reaction with Cs-modified zeolite]

Toluene disproportionation activity was examined by contacting the Cs-ZSM-5 zeolite of Example 11 with a toluene feed at 500° C. and WHSV of 3.5 $hr^{-1}$. Analysis of the reaction product revealed a selectivity to the para-isomer in the xylene product of 48.4%.

EXAMPLE 14

[Preparation of P-modified zeolite]

Two hundred grams of the ammonium form of ZSM-5 (65% on alumina binder) were added to a solution of 80 g of diammonium hydrogen phosphate in 300 ml of water. The mixture was allowed to stand at 90° C. for 2 hours, then the zeolite was removed by filtration, dried and calcined for 2 hours at 500° C. The P-ZSM-5 recovered contained 3.43 wt.% phosphorus.

EXAMPLE 15A

[Alkylation reaction with P-modified zeolite]

Alkylation of toluene with methanol was carried out by passing a toluene/methanol mixture in a molar ratio of 4/1 through 5.0 g of the P-ZSM-5 zeolite of Example 14 while heating at the desired temperature. The feed WHSV was 10. The results obtained at the various temperatures are shown below.

| Temperature °C. | Percent Toluene Conversion | Percent para-xylene in xylenes |
|---|---|---|
| 400 | 43.6 | 66.6 |
| 450 | 54.4 | 57.7 |
| 500 | 70.4 | 53.7 |
| 550 | 85.2 | 52.0 |
| 600 | 85.2 | 58.0 |

EXAMPLE 15B

In a similar manner, alkylation of toluene with ethylene was carried out by passing toluene and ethylene, at a weight hourly space velocity at 7.0 and 0.5, respectively, over the P-ZSM-5 at 400° C. Conversion of toluene was 74.8% and selectivity to p-ethyltoluene was 55.5%.

EXAMPLE 16

[Disproportionation reaction with P-modified zeolite]

Disproportionation of toluene was carried out by passing toluene over a 5.0 g of the P-ZSM-5 zeolite of Example 14 at a weight hourly space velocity of 3.5 and a temperature of between 475° C. and 550° C. The conditions and results are shown below.

| Temperature °C. | Toluene Conversion % | % Selectivity, mole | | % Para in Xylenes |
|---|---|---|---|---|
| | | Benzene | Xylene | |
| 475 | 14.9 | 52.8 | 47.6 | 39.1 |
| 500 | 27.1 | 53.3 | 45.4 | 35.1 |
| 525 | 37.4 | 56.1 | 42.2 | 32.1 |
| 550 | 44.0 | 60.4 | 37.3 | 30.1 |

EXAMPLE 17

[Preparation of Li-P-Modified Zeolite]

To a solution of 40 g lithium acetate in 10 ml water at 80° C. was added 6.0 g of the P-ZSM-5 of Example 14, and the mixture maintained at 80°–90° C. for 2 hours. After filtration and drying at about 90° C., the residue was calcined at 500° C. for 2 hours to give 6.2 g Li-P-ZSM-5. Analysis indicated the content of phosphorus to be 3.30%. The content of lithium was estimated to be 1.7%.

EXAMPLE 18

[Alkylation reaction with Li-P-modified zeolite]

Alkylation of toluene with methanol was carried out by passing a toluene/methanol mixture (molar ratio of 4/1) at WHSV=10 over 5.0 g of the Li-P-ZSM-5 catalyst of Example 17 at 500° C. Toluene conversion was 23.6% and selectivity to p-xylene in xylenes was 68.3%. At 600° C., these were measured at 44.8% and 74.4%, respectively. In contrast, the zeolite which had been modified with phosphorous alone demonstrated only a 53.7% selectivity to para-isomer at 500° C. and 58.0% at 600° C. (Example 15A).

EXAMPLE 19

[Preparation of K-P modified zeolte]

To a solution of 4.0 g potassium acetate in 10 ml water maintained at room temperature was added 6.0 g of the P-ZSM-5 of Example 14. The mixture was maintained at room temperature for 6 hours. After filtration and drying at about 90° C., the residue was calcined at 500° C. for 4 hours to give 6.0 g K-P-ZSM-5. Analysis indicated the content of potassium to be 9.57% and that of phorphorus to be 3.27%.

EXAMPLE 20

[Alkylation reaction with K-P-modified zeolite]

Ethylation of toluene was carried out by passing toluene (at WHSV=7) and ethylene (at WHSV=0.5) over 1.1 g of the K-P-ZSM-5 catalyst of Example 19 at 400° C. Conversion of toluene was 2.4% and selectivity to p-ethyltoluene in ethyltoluene was 72.8%. As seen from comparative Example 15B, in the same reaction the zeolite which had been modified with phosphorus (but not with potassium) demonstrated a selectivity to the para-isomer of only 55.5%.

EXAMPLE 21

[Disproportionation reaction with K-P-modified zeolite]

Disproportionation of toluene was carried out by passing toluene over 1.1 g of the K-P-ZSM-5 catalyst of Example 19 at WHSV=3.5 and 600° C. Toluene conversion was 0.5% and selectivity to p-xylene in xylene was 43%.

EXAMPLE 22

[Alkylation reaction with unmodified HZSM-11]

A toluene/methanol feed stream, at a 4/1 molar ratio, was passed over 2.0 g of HZSM-11 zeolite ($SiO_2/Al_2O_3$=70) at WHSV of 20 and at temperatures of 400°-600° C. The results are shown below.

| Temperature °C. | Percent Toluene Conversion | Percent Para-xylene in Xylenes |
|---|---|---|
| 400 | 67.6 | 23.4 |
| 500 | 90.4 | 24.0 |
| 600 | 157.2 | 22.7 |

EXAMPLE 23

[Preparation of Li-modified ZSM-11]

To a solution of 2.0 g lithium acetate in 5 ml water heated at 60° C. was added 1.5 g HZSM-11 having a $SiO_2/Al_2O_3$ ratio of 70. The mixture was maintained at 60°-70° C. for 2 hours. After filtration and drying at about 90° C. for 16 hours, the residue was calcined at 500° C. for 3 hours to give 1.51 g of Li-ZSM-11. The lithium content was found to be 2.97%.

EXAMPLE 24

[Alkylation reaction with Li-modified ZSM-11]

Alkylation of toluene with methanol was carried out by passing a toluene/methanol mixture (molar ratio of 4/1) at WHSV=10 over 1.1 g of the Li-ZSM-11 catalyst of Example 23 at 600° C. Toluene conversion was 1.25% and selectivity to p-xylene in xylenes was 31.1%.

It is to be understood that the foregoing is intended to be merely illustrative of certain specific embodiments of the disclosed invention. As those of skill in the art will readily appreciate, there are many variations which may be made on these specific embodiments without departing from the spirit of the invention described herein and such variations are clearly to be encompassed within the ambit of the following claims.

What is claimed is:

1. A catalyst composition comprising:
   a crystalline zeolite material characterized by a Constraint Index of within the approximate range of 1 to 12 and a silica to alumina mole ratio of at least 12;
   said catalyst composition further comprising at least 0.25 weight percent of one or more Group IA metals incorporated into said composition in the form of a Group IA metal oxide and at least 0.25 weight percent of phosphorus incorporated into said composition in the form of an oxide of phosphorus.

2. A catalyst composition comprising:
   a crystalline zeolite material selected from ZSM-5, ZSM-11, ZSM-12, ZSM-23, ZSM-35, ZSM-38 and ZSM-48;
   said catalyst composition further comprising at least 0.25 weight percent of one or more Group IA metals selected from lithium, potassium, sodium and cesium incorporated into said composition in the form of a Group IA metal oxide and at least 0.25 weight percent of phosphorus incorporated into said composition in the form of an oxide of phosphorus.

3. The composition of claim 2 wherein said Group IA metal is lithium.

4. The composition of claim 3 wherein said lithium comprises between 1 and 15 weight percent of said composition.

5. The composition of claim 2 wherein said Group IA metal is potassium.

6. The composition of claim 5 wherein said potassium comprises between 1 and 20 weight percent of said composition.

7. The composition of claim 2 wherein said Group IA metal is sodium.

8. A catalyst composition comprising:
   a crystalline zeolite material selected from ZSM-5, ZSM-11, ZSM-12, ZSM-23, ZSM-35, ZSM-38 and ZSM-48;
   said catalyst composition further comprising at least 0.25 weight percent of sodium incorporated into said composition in the form of sodium oxide and at least 0.25 weight percent of phosphorus incorporated into said composition in the form of an oxide of phosphorus.

9. The composition of claim 2, 3, 4, 5, 6, 7 or 8 wherein said zeolite is selected from the group consisting of ZSM-5 and ZSM-11.

10. The composition of claim 9 wherein said zeolite is ZSM-5.

11. The composition of claim 9 wherein said zeolite is admixed with a binder therefor.

* * * * *

UNITED STATES PATENT AND TRADEMARK OFFICE
CERTIFICATE OF CORRECTION

PATENT NO. : 4,391,739

DATED : July 5, 1983

INVENTOR(S) : Chin-Chiun Chu

It is certified that error appears in the above-identified patent and that said Letters Patent is hereby corrected as shown below:

Col. 7, line 12          "were" should be --where--.

Col. 8, line 27          "1976" should be --1967--.

Signed and Sealed this

Twenty-sixth Day of February 1985

[SEAL]

*Attest:*

DONALD J. QUIGG

*Attesting Officer*      *Acting Commissioner of Patents and Trademarks*